(12) United States Patent
Batchelor et al.

(10) Patent No.: US 10,456,191 B2
(45) Date of Patent: Oct. 29, 2019

(54) SURGICAL FORCEPS AND LATCHING SYSTEM

(71) Applicant: GYRUS ACMI, INC., Southborough, MA (US)

(72) Inventors: Kester J Batchelor, Mound, MN (US); Richard J Curtis, Maple Grove, MN (US); Ryan J Windgassen, Nowthen, MN (US)

(73) Assignee: GYRUS ACMI, INC., Southborough, MA (US)

( * ) Notice: Subject to any disclaimer, the term of this patent is extended or adjusted under 35 U.S.C. 154(b) by 819 days.

(21) Appl. No.: 14/829,725

(22) Filed: Aug. 19, 2015

(65) Prior Publication Data

US 2016/0051273 A1 Feb. 25, 2016

Related U.S. Application Data

(60) Provisional application No. 62/039,506, filed on Aug. 20, 2014.

(51) Int. Cl.
*A61B 18/14* (2006.01)
*A61B 17/28* (2006.01)
(Continued)

(52) U.S. Cl.
CPC ...... *A61B 18/1442* (2013.01); *A61B 17/2812* (2013.01); *A61B 17/2833* (2013.01); *A61B 17/295* (2013.01); *A61B 18/085* (2013.01); *A61B 18/1402* (2013.01); *A61B 17/282* (2013.01); *A61B 2017/00411* (2013.01);
(Continued)

(58) Field of Classification Search
CPC ............ A61B 18/1442; A61B 17/2812; A61B 17/295; A61B 17/282; A61B 2017/00411; A61B 18/085; A61B 18/1402; A61B 2018/00273; A61B 2018/00607;
(Continued)

(56) References Cited

U.S. PATENT DOCUMENTS 1,198,958 A 9/1916 Risely
2,042,985 A 6/1936 Gardella
(Continued)

FOREIGN PATENT DOCUMENTS

CN 1149519 A 5/1997
CN 102164556 8/2011
(Continued)

OTHER PUBLICATIONS

315MHZ sliding remote cover, available at website : http://www.aliexpress.com/item/Sliding-Cover-Gate-Remote-Control-Duplicator-Adjustable-Frequency-Remote-Copy-100pCS-lot-Free-Shipping-by-DHL/566451354.html?tracelog=back_to_detail_a (accessed on Feb. 21, 2013).
(Continued)

*Primary Examiner* — Jaymi E Della
(74) *Attorney, Agent, or Firm* — The Dobrusin Law Firm, PC

(57) ABSTRACT

A surgical forceps comprising: a first working arm and a second working arm configured to move towards and away from each other; and an electromagnetic latching system; wherein the electromagnetic latching system is configured to create a force that is in a direction aligned with closing of the forceps or opposite to the closing of the forceps when an electromagnetic activation button is depressed.

19 Claims, 4 Drawing Sheets

(51) Int. Cl.
*A61B 17/295* (2006.01)
*A61B 18/08* (2006.01)
*A61B 18/00* (2006.01)
*A61B 17/00* (2006.01)

(52) U.S. Cl.
CPC .............. *A61B 2018/00273* (2013.01); *A61B 2018/00607* (2013.01); *A61B 2018/00946* (2013.01); *A61B 2018/00958* (2013.01); *A61B 2018/1412* (2013.01); *A61B 2018/1455* (2013.01); *A61B 2018/1462* (2013.01)

(58) Field of Classification Search
CPC .... A61B 2018/1412; A61B 2018/1455; A61B 2018/146
See application file for complete search history.

(56) References Cited

U.S. PATENT DOCUMENTS

| | | |
|---|---|---|
| 2,214,984 A | 9/1940 | Bachmann |
| 2,381,084 A | 8/1945 | Slad |
| 2,575,652 A | 11/1951 | Bovee |
| 2,894,424 A | 7/1959 | Vaughan, Jr. |
| 3,399,583 A | 9/1968 | Hall |
| 3,417,752 A | 12/1968 | Butler |
| 3,465,621 A | 9/1969 | Ladd |
| 3,576,072 A | 4/1971 | Foster |
| 3,643,663 A | 2/1972 | Sutter |
| 3,685,518 A | 8/1972 | Beuerle et al. |
| 3,699,632 A | 10/1972 | Anhalt |
| 3,818,784 A | 6/1974 | McClure |
| 3,913,586 A | 10/1975 | Baumgarten |
| 4,041,952 A | 8/1977 | Morrison, Jr. et al. |
| 4,154,226 A | 5/1979 | Hennig et al. |
| 4,171,700 A | 10/1979 | Farin |
| 4,202,337 A | 5/1980 | Hren et al. |
| 4,318,313 A | 3/1982 | Tartaglia |
| 4,375,218 A | 3/1983 | DiGeronimo |
| 4,407,069 A | 10/1983 | Conners |
| 4,418,692 A | 12/1983 | Guay |
| 4,443,935 A | 4/1984 | Zamba et al. |
| 4,463,759 A | 7/1984 | Garito et al. |
| 4,492,231 A | 1/1985 | Auth |
| 4,492,832 A | 1/1985 | Taylor |
| 4,494,543 A | 1/1985 | Hart |
| 4,504,707 A | 3/1985 | Ochiai |
| 4,524,648 A | 6/1985 | Chung |
| 4,552,143 A | 11/1985 | Lottick |
| 4,655,215 A | 4/1987 | Pike |
| 4,669,470 A | 6/1987 | Brandfield |
| 4,686,980 A | 8/1987 | Williams et al. |
| 4,713,885 A | 12/1987 | Keklak et al. |
| 4,757,612 A | 7/1988 | Peyrot |
| 4,784,136 A | 11/1988 | Klein |
| 4,860,745 A | 8/1989 | Farin et al. |
| 4,896,661 A | 1/1990 | Bogert et al. |
| 4,935,027 A | 6/1990 | Yoon |
| 5,021,616 A | 6/1991 | Hardt |
| 5,035,695 A | 7/1991 | Weber, Jr. et al. |
| 5,071,426 A | 12/1991 | Dolgin et al. |
| 5,104,397 A | 4/1992 | Vasconcelos et al. |
| 5,108,392 A | 4/1992 | Spingler |
| 5,147,378 A | 9/1992 | Markham |
| 5,176,702 A | 1/1993 | Bales et al. |
| 5,190,541 A | 3/1993 | Abele et al. |
| 5,196,009 A | 3/1993 | Kirwan, Jr. |
| 5,207,691 A | 5/1993 | Nardella |
| 5,207,696 A | 5/1993 | Matwijcow |
| 5,208,983 A | 5/1993 | Masse |
| 5,226,904 A | 7/1993 | Gentelia et al. |
| 5,281,216 A | 1/1994 | Klicek |
| 5,290,286 A | 3/1994 | Parins |
| 5,293,878 A | 3/1994 | Bales et al. |
| 5,318,589 A | 6/1994 | Lichtman |
| 5,342,359 A | 8/1994 | Rydell |
| 5,370,659 A | 12/1994 | Sakashita |
| 5,403,312 A | 4/1995 | Yates et al. |
| 5,413,575 A | 5/1995 | Haenggi |
| 5,423,814 A | 6/1995 | Zhu et al. |
| 5,425,743 A | 6/1995 | Nicholas |
| 5,440,813 A | 8/1995 | Roskam |
| 5,441,498 A | 8/1995 | Perkins |
| 5,443,463 A | 8/1995 | Stern et al. |
| 5,456,695 A | 10/1995 | Herve Dallemagne |
| 5,458,598 A | 10/1995 | Fienberg et al. |
| 5,472,442 A | 12/1995 | Klicek |
| 5,483,952 A | 1/1996 | Aranyi |
| 5,484,435 A | 1/1996 | Fleenor et al. |
| 5,499,998 A | 3/1996 | Meade |
| 5,531,744 A | 7/1996 | Nardella et al. |
| 5,540,685 A | 7/1996 | Parins et al. |
| 5,562,503 A | 10/1996 | Ellman et al. |
| 5,573,424 A | 11/1996 | Poppe |
| 5,626,577 A | 5/1997 | Harris |
| 5,626,578 A * | 5/1997 | Tihon .................. A61B 18/1442 606/48 |
| 5,658,281 A | 8/1997 | Heard |
| 5,661,100 A * | 8/1997 | Minami .............. B41M 5/3333 503/208 |
| 5,665,100 A * | 9/1997 | Yoon ..................... A61B 10/06 606/139 |
| 5,693,052 A | 12/1997 | Weaver |
| 5,702,390 A | 12/1997 | Austin et al. |
| 5,709,680 A | 1/1998 | Yates et al. |
| 5,735,849 A | 4/1998 | Baden et al. |
| 5,779,701 A | 7/1998 | McBrayer et al. |
| 5,810,805 A | 9/1998 | Sutcu et al. |
| 5,827,281 A | 10/1998 | Levin |
| 5,884,954 A | 3/1999 | Trozera |
| 5,891,140 A | 4/1999 | Ginn et al. |
| 5,902,301 A | 5/1999 | Olig |
| 5,922,001 A | 7/1999 | Yoon |
| 5,951,545 A | 9/1999 | Schilling et al. |
| 6,024,741 A | 2/2000 | Williamson, IV et al. |
| 6,030,384 A | 2/2000 | Nezhat |
| 6,039,734 A | 3/2000 | Goble |
| 6,050,996 A | 4/2000 | Schmaltz et al. |
| 6,053,908 A | 4/2000 | Crainich et al. |
| 6,074,386 A | 6/2000 | Goble et al. |
| 6,102,909 A | 8/2000 | Chen et al. |
| 6,110,171 A | 8/2000 | Rydell |
| 6,113,596 A | 9/2000 | Hooven et al. |
| 6,117,158 A | 9/2000 | Measamer et al. |
| 6,117,169 A | 9/2000 | Moe |
| 6,152,923 A | 11/2000 | Ryan |
| 6,190,386 B1 | 2/2001 | Rydell |
| 6,270,497 B1 | 8/2001 | Sekino et al. |
| 6,273,887 B1 | 8/2001 | Yamauchi et al. |
| 6,325,795 B1 | 12/2001 | Lindemann et al. |
| 6,355,032 B1 | 3/2002 | Hovda et al. |
| 6,358,268 B1 | 3/2002 | Hunt et al. |
| 6,402,747 B1 | 6/2002 | Lindemann et al. |
| 6,428,538 B1 | 8/2002 | Blewett et al. |
| 6,458,128 B1 | 10/2002 | Schulze |
| 6,464,704 B2 | 10/2002 | Schmaltz et al. |
| 6,486,419 B2 | 11/2002 | Horiguchi et al. |
| 6,494,886 B1 | 12/2002 | Wilk et al. |
| 6,514,252 B2 | 2/2003 | Nezhat et al. |
| 6,551,313 B1 | 4/2003 | Levin |
| 6,585,735 B1 | 7/2003 | Frazier et al. |
| 6,619,038 B2 | 9/2003 | Takada et al. |
| 6,623,499 B1 | 9/2003 | Andreini et al. |
| 6,641,595 B1 | 11/2003 | Moran et al. |
| 6,652,514 B2 | 11/2003 | Ellman et al. |
| 6,679,882 B1 | 1/2004 | Kornerup |
| 6,689,130 B2 | 2/2004 | Arai et al. |
| 6,695,840 B2 | 2/2004 | Schulze |
| 6,726,686 B2 | 4/2004 | Buysse et al. |
| 6,749,610 B2 | 6/2004 | Kirwan, Jr. et al. |
| 6,752,767 B2 | 6/2004 | Turovskiy et al. |
| 6,773,434 B2 | 8/2004 | Ciarrocca |
| 6,808,525 B2 | 10/2004 | Latterell et al. |
| 6,827,717 B2 | 12/2004 | Brommersma et al. |

(56) References Cited

U.S. PATENT DOCUMENTS

| | | |
|---|---|---|
| 6,860,882 B2 | 3/2005 | Battles et al. |
| 6,926,716 B2 | 8/2005 | Baker et al. |
| 6,942,662 B2 | 9/2005 | Goble et al. |
| 7,083,613 B2 | 8/2006 | Treat |
| 7,094,231 B1 | 8/2006 | Ellman et al. |
| 7,108,694 B2 | 9/2006 | Miura et al. |
| 7,112,199 B2 | 9/2006 | Cosmescu |
| 7,147,637 B2 | 12/2006 | Goble |
| 7,147,638 B2 | 12/2006 | Goble |
| 7,150,749 B2 | 12/2006 | Dycus et al. |
| 7,156,846 B2 | 1/2007 | Dycus et al. |
| 7,232,440 B2 | 6/2007 | Dumbauld et al. |
| 7,244,257 B2 | 7/2007 | Podhajsky et al. |
| 7,252,667 B2 | 8/2007 | Moses et al. |
| 7,344,536 B1 | 3/2008 | Lunsford et al. |
| 7,367,976 B2 | 5/2008 | Lawes et al. |
| 7,377,902 B2 | 5/2008 | Burbank |
| 7,481,810 B2 | 1/2009 | Dumbauld et al. |
| 7,503,917 B2 | 3/2009 | Sartor et al. |
| 7,604,635 B2 | 10/2009 | McClurken et al. |
| 7,625,391 B2 | 12/2009 | Kebel et al. |
| 7,674,261 B2 | 3/2010 | Garito et al. |
| 7,686,827 B2 | 3/2010 | Hushka |
| 7,722,607 B2 | 5/2010 | Dumbauld et al. |
| 7,753,909 B2 | 7/2010 | Chapman et al. |
| 7,758,577 B2 | 7/2010 | Nobis et al. |
| 7,789,878 B2 | 9/2010 | Dumbauld et al. |
| 7,879,035 B2 | 2/2011 | Garrison et al. |
| 7,896,875 B2 | 3/2011 | Heim et al. |
| 7,909,820 B2 | 3/2011 | Lipson et al. |
| 7,922,718 B2 | 4/2011 | Moses et al. |
| 7,931,649 B2 | 4/2011 | Couture et al. |
| 7,931,668 B2 | 4/2011 | Sloat |
| 7,938,469 B2 | 5/2011 | Ait-Mani |
| 7,942,872 B2 | 5/2011 | Ein-Gal |
| 7,955,331 B2 | 6/2011 | Truckai et al. |
| 7,998,140 B2 | 8/2011 | McClurken et al. |
| 8,062,292 B1 | 11/2011 | Slater |
| 8,100,894 B2 | 1/2012 | Mucko et al. |
| 8,162,940 B2 | 4/2012 | Johnson et al. |
| 8,216,231 B2 | 7/2012 | Behl et al. |
| 8,226,649 B2 | 7/2012 | Falkenstein et al. |
| 8,246,094 B2 | 8/2012 | Long et al. |
| 8,251,989 B1 | 8/2012 | Newton et al. |
| 8,262,655 B2 | 9/2012 | Ghabrial et al. |
| 8,267,935 B2 | 9/2012 | Couture et al. |
| 8,328,170 B2 | 12/2012 | Wasinger |
| 8,361,065 B2 | 1/2013 | West et al. |
| 8,361,072 B2 | 1/2013 | Dumbauld et al. |
| 8,485,413 B2 | 7/2013 | Scheib et al. |
| 8,491,626 B2 | 7/2013 | Roy et al. |
| 8,496,603 B2 | 7/2013 | Mamourian |
| 8,568,411 B2 | 10/2013 | Falkenstein et al. |
| 8,628,529 B2 | 1/2014 | Aldridge et al. |
| 8,632,553 B2 | 1/2014 | Sakamoto et al. |
| 8,702,691 B2 | 4/2014 | Weber et al. |
| 8,702,700 B2 | 4/2014 | Maeda et al. |
| 8,882,756 B2 | 11/2014 | Greeley et al. |
| 8,939,972 B2 | 1/2015 | Twomey |
| 9,023,035 B2 | 5/2015 | Allen et al. |
| 9,204,879 B2 | 12/2015 | Shelton |
| 9,320,563 B2 | 4/2016 | Brustad et al. |
| 9,326,810 B2 | 5/2016 | Shilev et al. |
| 9,358,065 B2 | 6/2016 | Ladtkow et al. |
| 9,439,665 B2 | 9/2016 | Marczyk et al. |
| 9,452,011 B2 | 9/2016 | Batchelor et al. |
| 2002/0106609 A1 | 8/2002 | Palermo et al. |
| 2002/0107517 A1 | 8/2002 | Witt et al. |
| 2002/0115997 A1 | 8/2002 | Truckai et al. |
| 2002/0173787 A1* | 11/2002 | Buysse ............ A61B 18/1442 606/51 |
| 2003/0018329 A1 | 1/2003 | Hooven |
| 2003/0144652 A1 | 1/2003 | Baker et al. |
| 2003/0050633 A1 | 3/2003 | Ellman |
| 2003/0097126 A1 | 5/2003 | Woloszko |
| 2003/0105474 A1* | 6/2003 | Bonutti ............... A61B 17/04 606/139 |
| 2003/0109876 A1 | 6/2003 | Yamauchi |
| 2003/0114850 A1 | 6/2003 | McClurken et al. |
| 2003/0181904 A1 | 9/2003 | Levine et al. |
| 2004/0030330 A1 | 2/2004 | Brassell et al. |
| 2004/0082946 A1 | 4/2004 | Malis |
| 2004/0097117 A1 | 5/2004 | Gonnering |
| 2005/0065510 A1 | 3/2005 | Carmel et al. |
| 2005/0113824 A1 | 5/2005 | Sartor |
| 2005/0113825 A1 | 5/2005 | Cosmescu |
| 2005/0113827 A1 | 5/2005 | Dumbauld et al. |
| 2005/0159745 A1 | 7/2005 | Truckai et al. |
| 2005/0187512 A1 | 8/2005 | Isola et al. |
| 2005/0216019 A1 | 9/2005 | Eckman |
| 2006/0084973 A1 | 4/2006 | Hushka |
| 2006/0089670 A1* | 4/2006 | Hushka ............ A61B 17/2833 606/205 |
| 2006/0190035 A1 | 8/2006 | Hushka et al. |
| 2006/0217701 A1 | 9/2006 | Young et al. |
| 2007/0049922 A1 | 3/2007 | Rontal |
| 2007/0078458 A1 | 4/2007 | Dambauld et al. |
| 2007/0093857 A1 | 4/2007 | Rogers et al. |
| 2007/0123855 A1 | 5/2007 | Morley et al. |
| 2007/0129716 A1 | 6/2007 | Daw |
| 2007/0179491 A1 | 8/2007 | Kratoska et al. |
| 2008/0033428 A1 | 2/2008 | Artale et al. |
| 2008/0058845 A1* | 3/2008 | Shimizu ............... A61B 17/29 606/169 |
| 2008/0077129 A1 | 3/2008 | Van Wyk et al. |
| 2008/0147092 A1 | 6/2008 | Rogge et al. |
| 2008/0154300 A1 | 6/2008 | Jabbour |
| 2008/0236860 A1 | 10/2008 | Howe |
| 2008/0287948 A1 | 11/2008 | Newton et al. |
| 2009/0062786 A1 | 3/2009 | Garito et al. |
| 2009/0062792 A1 | 3/2009 | Vakharia et al. |
| 2009/0093804 A1 | 4/2009 | Newton |
| 2009/0138003 A1 | 5/2009 | DeVille et al. |
| 2009/0138013 A1 | 5/2009 | Thorne et al. |
| 2009/0192509 A1 | 7/2009 | Curtis |
| 2009/0248002 A1 | 10/2009 | Takashino et al. |
| 2010/0042096 A1 | 2/2010 | Ellman |
| 2010/0087814 A1 | 4/2010 | Desinger et al. |
| 2010/0137854 A1 | 6/2010 | Hosier |
| 2010/0228249 A1 | 9/2010 | Mohr |
| 2011/0045680 A1 | 2/2011 | Beller |
| 2011/0054462 A1 | 3/2011 | Ellman |
| 2011/0077648 A1 | 3/2011 | Lee et al. |
| 2011/0112530 A1 | 5/2011 | Keller |
| 2011/0178515 A1 | 7/2011 | Bloom et al. |
| 2011/0224669 A1 | 9/2011 | Podany |
| 2011/0251613 A1 | 10/2011 | Guerra et al. |
| 2011/0319892 A1 | 12/2011 | Blomeyer |
| 2012/0022530 A1 | 1/2012 | Woodruff et al. |
| 2012/0078292 A1 | 3/2012 | Banju |
| 2012/0095460 A1 | 4/2012 | Rooks et al. |
| 2012/0101501 A1 | 4/2012 | Nishimura et al. |
| 2012/0123405 A1 | 5/2012 | Moua et al. |
| 2012/0150165 A1 | 6/2012 | Conley |
| 2012/0202388 A1 | 8/2012 | Selig |
| 2013/0023874 A1 | 1/2013 | Lawes et al. |
| 2013/0066317 A1 | 3/2013 | Evans et al. |
| 2013/0079762 A1 | 3/2013 | Twomey et al. |
| 2013/0144284 A1* | 6/2013 | Behnke, II ......... A61B 18/1815 606/33 |
| 2013/0178852 A1 | 7/2013 | Allen, IV et al. |
| 2013/0237982 A1 | 9/2013 | Rencher et al. |
| 2013/0296846 A1 | 11/2013 | Canady et al. |
| 2014/0100569 A1 | 4/2014 | Lawes et al. |
| 2014/0236202 A1 | 8/2014 | Palmer et al. |
| 2014/0276772 A1 | 9/2014 | Batchelor et al. |
| 2014/0276785 A1 | 9/2014 | Batchelor et al. |
| 2014/0276786 A1 | 9/2014 | Batchelor |
| 2014/0276794 A1 | 9/2014 | Batchelor et al. |
| 2014/0276795 A1 | 9/2014 | Batchelor et al. |
| 2014/0276796 A1 | 9/2014 | Batchelor et al. |
| 2014/0276797 A1 | 9/2014 | Batchelor et al. |
| 2014/0276798 A1 | 9/2014 | Batchelor et al. |
| 2014/0276799 A1 | 9/2014 | Batchelor et al. |

(56) References Cited

U.S. PATENT DOCUMENTS

| | | |
|---|---|---|
| 2014/0276800 A1 | 9/2014 | Batchelor et al. |
| 2014/0276804 A1 | 9/2014 | Batchelor |
| 2015/0119885 A1 | 4/2015 | Windgassen et al. |
| 2015/0148798 A1 | 5/2015 | Windgassen et al. |
| 2015/0320485 A1 | 11/2015 | Batchelor et al. |

FOREIGN PATENT DOCUMENTS

| | | |
|---|---|---|
| CN | 102836006 | 12/2012 |
| EP | 0392548 A1 | 10/1994 |
| EP | 1089664 | 4/2001 |
| EP | 1769765 A1 | 4/2007 |
| EP | 1530952 A1 | 7/2007 |
| EP | 1810629 A1 | 7/2007 |
| EP | 1977706 A1 | 10/2008 |
| EP | 2403422 | 1/2012 |
| JP | H10-137259 A | 5/1998 |
| JP | H10-504485 A | 5/1998 |
| JP | 2000070280 A | 3/2000 |
| JP | 2001170070 A | 6/2001 |
| JP | 2004508875 A | 3/2004 |
| JP | 2005144192 A | 6/2005 |
| JP | 2005521465 A | 7/2005 |
| JP | 2009247893 A | 10/2009 |
| JP | 2012518490 A | 8/2012 |
| WO | 96/005776 A1 | 2/1996 |
| WO | 9966850 | 12/1999 |
| WO | 02/24089 A1 | 3/2002 |
| WO | 2006/122279 | 11/2006 |
| WO | 2007/002545 | 1/2007 |
| WO | 2007/093857 | 8/2007 |
| WO | 2010/101897 | 9/2010 |
| WO | 2012/053530 A | 4/2012 |
| WO | 2014/096815 A2 | 6/2014 |

OTHER PUBLICATIONS

Potentially related U.S. Appl. No. 14/589,482, filed Jan. 5, 2015 published as 2015/0148798 on May 28, 2015.
Potentially related U.S. Appl. No. 14/589,515, filed Jan. 5, 2015, published as 2015/0119885 on Apr. 30, 2015.
Potentially related U.S. Appl. No. 14/830,069, filed Aug. 19, 2015.
Potentially related U.S. Appl. No. 14/830,255, filed Aug. 19, 2015.
Potentially related U.S. Appl. No. 14/177,780, filed Feb. 11, 2014, published as 2014/0276794 on Sep. 18, 2014.
Potentially related U.S. Appl. No. 14/178,411, filed Feb. 12, 2014, published as 2014/0276785 on Sep. 18, 2014.
Potentially related U.S. Appl. No. 14/178,569, filed Feb. 12, 2014, published as 2014/0276804 on Sep. 18, 2014.
Potentially related U.S. Appl. No. 14/178,577, filed Feb. 12, 2014, published as 2014/0276786 on Sep. 18, 2014.
Potentially related U.S. Appl. No. 14/205,598, filed Mar. 12, 2014, published as 2014/0276795 on Sep. 18, 2014.
Potentially related U.S. Appl. No. 14/205,919, filed Mar. 12, 2014 published as 2014/0276796 on Sep. 18, 2014.
Potentially related U.S. Appl. No. 14/209,071, filed Mar. 13, 2014 published as 2014/0276798 on Sep. 18, 2014.
Potentially related U.S. Appl. No. 14/210,535, filed Mar. 14, 2014, published as 2014/0276799 on Sep. 18, 2014.
Potentially related U.S. Appl. No. 14/210,741, filed Mar. 14, 2014, published as 2014/0276800 on Sep. 18, 2104.
Potentially related U.S. Appl. No. 14/211,042, filed Mar. 14, 2014, published as 2014/0276772 on Sep. 18, 2014.
Potentially related to U.S. Appl. No. 14/206,010, filed Mar. 12, 2014, published as 2014/0276797 on Sep. 18, 2014.
Sliding Gate Remote Control Duplicator, available at website: http://www.aliexpress.com/item/315MHZ-sliding-cover-remote-controller-duplicating-remote-controller-sliding-gate-remote-garager-door-remote/491795542.html (accessed on Feb. 21, 2013).
International Search Report and Written Opinion for Application No. PCT/US2015/045788 dated Nov. 3, 2015.

* cited by examiner

SURGICAL FORCEPS AND LATCHING SYSTEM

FIELD

The present teachings generally relate to surgical forceps with a latch system that secures the forceps in an open position, a closed position, or assists in biasing the forceps, and more specifically surgical forceps that are configured as an electrosurgical device with an electromagnetic latching system.

BACKGROUND

Typically, surgical forceps have one configuration where the electrosurgical device performs a single function. More recently, forceps have been introduced as electrosurgical devices that can be switched between two configurations and can apply two different therapy currents. These devices have a configuration where the device is configured as forceps and can be used to grip anatomical features and includes a configuration where the device can be uses as a surgical pencil. The surgeon in using these devices apply pressure to the forceps and may be required to hold the pressure for several seconds to a minute. By repeatedly gripping and holding the forceps closed the surgeon's fingers may become tired or strained. Further in order to switch between the forceps configuration and the pencil configuration the surgeon is required to close the forceps while locking the device in the pencil configuration, which adds further strain to the surgeon's hands. Finally, while using the forceps to grip items the amount of force required to move the forceps may be hard for some surgeons and relatively easy for other surgeons. This may result in some surgeons thinking that the forceps are mushy and other surgeons thinking that the forceps are too rigid.

Examples of some electrosurgical instruments may be found in U.S. Pat. Nos. 6,110,171; 6,113,596; 6,190,386; 6,358,268; and 7,232,440; and U.S. Patent Application Publication Nos. 2005/0113827; 2005/0187512; 2006/0084973; 2012/0123405; 2014/0276795; and 2014/0276799 all of which are incorporated by reference herein for all purposes. It would be attractive to have an electrosurgical device includes a latching system that assists in holding the device in a closed position. It would be attractive to have an electrosurgical device that selectively closes the forceps and grips an anatomical feature while a therapy current is being applied. What is needed is an electrosurgical device that includes an electromagnetic latching system that assists in closing or opening the electrosurgical device while the electrosurgical device is configured as forceps. What is needed is an electrosurgical device that includes an electromagnetic latching system that selectively moves the forceps so that the amount of grip strength required to open and close the forceps can be varied for each user. What is needed is an electrosurgical device that used one or more electromagnetic latches to move the arms of the forceps so that the arms are opened, closed, locked, unlocked, or a combination thereof.

SUMMARY

The present teachings meet one or more of the present needs by providing: A surgical forceps comprising: a first working arm and a second working arm configured to move in a direction that is towards and away from each other in a manner that creates a resilient moving force; an electromagnetic latching system; wherein the electromagnetic latching system is configured to create one or more of the following: (i) a force that is superimposed upon the resilient moving force so that the force biases the first working arm, the second working arm, or both in a direction of the resilient moving force when an electromagnetic activation button is depressed; (ii) an adjustable force that is superimposed upon the resilient moving force when an electromagnetic activation button is depressed; (iii) a force that is superimposed upon the resilient moving force so that the force biases the first working arm, the second working arm, or both in an opposite direction as the resilient moving force when an electromagnetic activation button is depressed; or (iv) a force that latches the first working arm and second working arm together and a bipolar current that extends between the first working arm and the second working arm when a first activation button is energized.

Another possible embodiment of the present teachings comprises: a surgical forceps comprising: a first working arm and a second working arm configured to move towards and away from each other; and an electromagnetic latching system; wherein the electromagnetic latching system is configured to create a force that is in a direction aligned with closing of the forceps or opposite to the closing of the forceps when an electromagnetic activation button is depressed.

The teachings herein provide an electrosurgical device includes a latching system that assists in holding the device in a closed position. The teachings herein provide an electrosurgical device that selectively closes the forceps and grips an anatomical feature while a therapy current is being applied. The teachings herein provide an electrosurgical device that includes an electromagnetic latching system that assists in closing or opening the electrosurgical device while the electrosurgical device is configured as forceps. The teachings herein provide an electrosurgical device that includes an electromagnetic latching system that selectively moves the forceps so that the amount of grip strength required to open and close the forceps can be varied for each user. The teachings herein provide an electrosurgical device that used one or more electromagnetic latches to move the arms of the forceps so that the arms are opened, closed, locked, unlocked, or a combination thereof.

DETAILED DESCRIPTION

Figure 1:
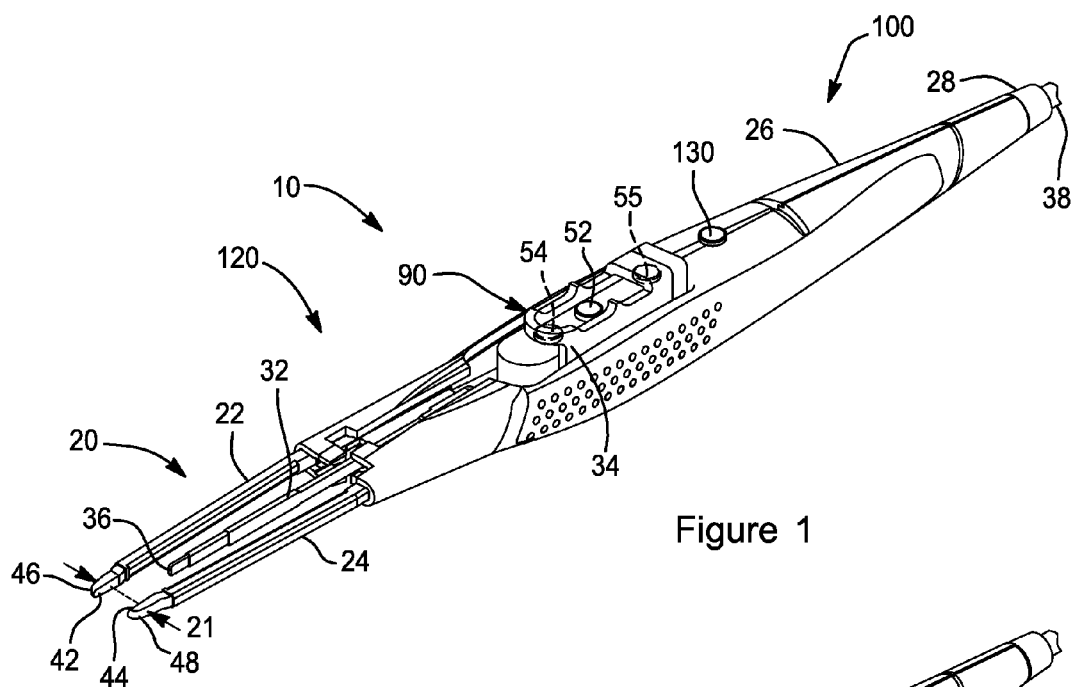
FIG. 1 illustrates an electrosurgical device in a first configuration.

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The present application claims priority to U.S. Provisional Patent Application Ser. No. 62/039,506, filed on Aug. 20, 2014, the contents of which are both incorporated by reference herein in their entirety for all reasons. The present teachings generally relate to surgical forceps. The forceps may function to grip, hold, squeeze, or a combination thereof one or more objects. The forceps may include one or more finger grips (i.e., configured like scissors) that may be used to move the forceps so that the forceps may be used to grip one or more objects. The forceps may be free of finger grips and be actuated by direct pressure being applied to opposing sides of the forceps so that the forceps close and grip an object. The forceps include at least two working arms (e.g., a first working arm and a second working arm).

The working arms (or jaws) may function to grip, hold, squeeze, or a combination thereof an object when the object is between the two or more opposing working arms. The working arms may include one or more gripping features that may assist in gripping, holding, squeezing, or a combination thereof an object. The working arms may be generally straight. The working arms may be arcuate or include an arc. The working arms may be flexible. The working arms may include a bow that may be compressed during gripping and may assist moving the working arms apart, may create a resilient moving force, or both. The working arms may be movable between two or more positions. Preferably, the working arms are movable between at least a first position and a second position. For example, the working arms may be movable between a bipolar configuration (e.g., first position) and a monopolar configuration (e.g., second position). The working arms may be used in electrosurgery and may be used to apply power to one or more features of interest. The working arms in the first position may be off, energized, one working arm may be energized, or a combination thereof. The working arms in the second position may be off, one or both of the working arms may be electrically disconnected, one or both of the working arms may be electrically connected, one working arm may be shorted by the other working arm, or a combination thereof. More preferably, in the second position the working arms are immobilized so that the working arms cannot be used a forceps. The working arms may be longitudinally static and moveable relative to each other. The working arms may be longitudinally moveable and may be moveable relative to each other so that a gripping force may be created. For example, the working arms when in a bipolar configuration may both be extended and then retracted so that a blade electrode (i.e., a point on the blade where energy enters or exits the blade) may be exposed forming a monopolar configuration (i.e., longitudinally movable). Preferably, the working arms are longitudinally static and laterally movable (i.e., movable towards and away from each other). The working arms may be rotationally static (i.e., may not rotate about their longitudinal axis). The working arms may be movable so that tip regions of the working arms are moved into contact with each other.

The working arms include a tip region. The tip regions function to grip features of interest, apply power to features of interest, or both. The tip region may include a portion that is configured to assist in facilitating gripping, holding, squeezing, or a combination thereof. Additionally, the tip region may be configured in one or more electrosurgical configurations (e.g., a monopolar configuration, bipolar configuration, or a combination of both). The tip region may be the distal most portion of the working arms. Each of the working arms may include an electrode (e.g., a first working arm includes a first electrode and the second working arm includes a second electrode). The tip region may include teeth, serrations, mouse teeth, be free of teeth (i.e., smooth), or a combination thereof. The tip region may be fully and/or partially insulated. Preferably, the tip region includes insulation on the non-contact portions of the working arms so that electrosurgical energy is not transferred through incidental contact. The working arms may include an active portion and an inactive portion (i.e., an insulated portion). Each of the working arms may be connected by a central section, a pivot point, movable connection, or a combination thereof.

The central section may function create a central connection location, a movable connection, or both between the working arms. The central section may connect to an end of each working arm and the working arms may extend cantilever from the central section. The central section may be a portion that the user grips. The central section may be a main body portion of a handpiece. The central section may include a pivot point, a pivot pin, a movable connection, or a combination thereof that the working arms rotate about. The central section may be located between a proximal end and distal end of the handpiece, surgical forceps, electrosurgical device, or a combination thereof.

The handpiece may be any part of the device that the user grips, that houses one or more of the control buttons, one or more switches, one or more electrical connectors, one or more diodes, one or more capacitors, or a combination thereof. The handpiece may house all or a portion of the control circuitry, a central processing unit, or both. The handpiece may house or include an electromagnetic latching system, securing mechanism, one or more electromagnetic latches, or a combination thereof. The handpiece may electrically connect the electrosurgical device, the electrical system, the surgical forceps, or a combination thereof to the generator or a power source. The handpiece may both physically connect the functional elements of the electrosurgical device and electrically connect the elements of the electrosurgical device. Preferably, the handpiece is the portion of the forceps that a surgeon grips. More preferably, the handpiece is a central portion that includes both buttons and one or more electrical connectors for supplying power to the forceps, electrosurgical device, the working arms, the blade, electromagnetic latching system, electromagnetic activation buttons, or a combination thereof. The handpiece may include one or more movable members, one or more handpiece components, one or more electromagnetic latches, one or more movement mechanism, or a combination thereof.

The one or more activation buttons may function to control one or more functions of the electrosurgical device. The one or more activation buttons may control the bipolar power, the monopolar power, a bipolar cut setting, bipolar coagulation setting, a therapy current, rotation of the blade, rotation of the monopolar electrode, the electromagnetic latching system, the first electromagnetic latch, the second electromagnetic latch, or a combination thereof. The one or more activation buttons may be one or more electromagnetic activation buttons. The one or more electromagnetic activation buttons may move the working arms apart, together, or both. The one or more electromagnetic activation buttons may lock the working arms in a predetermined position. The one or more electromagnetic activation buttons may be located on a top of the forceps, electrosurgical device, handpiece, or a combination thereof where a user does not grip. The electromagnetic activation buttons may be located in a gripping region. The electromagnetic activation buttons may be located in the gripping region so that the user may move the forceps without the electromagnetic latching system, but may activate the electromagnetic latching system without any repositioning or movement on the forceps, electrosurgical device, handpiece, or a combination thereof. The electromagnetic activation buttons may be located in the gripping section and may vary the magnitude of force applied depending on the amount of force applied by a user. For example, the more pressure a user applies to the forceps the more pressure the electromagnetic latching system may apply. The magnitude of force applied by the electromagnetic latching system may be irrelevant to the amount of pressure applied to the electromagnetic activation buttons. The one or more electromagnetic activation buttons may control the amount of force required to move the working arms. For example, the working arms without the electromagnetic latching system may require 30 N of force to close. One of the electromagnetic activation buttons may vary this force by assisting the surgeon in moving the working arms. For example, the amount of force required may be reduced from 30 N of force to 10 N of force to move the working arms. The magnitude of force applied by the electromagnetic latching system may be varied by a measured impedance. The activation button that assists in adjusting the amount of force required to move the working arms may be a selector switch, but is preferably a dial that allows a user to increase or decrease the amount or magnitude of assistance provided. The handpiece, forceps, electrosurgical device, or a combination thereof may include only one electromagnetic activation button, but preferably includes a plurality of electromagnetic activation buttons. In addition to including electromagnetic activation buttons the forceps, electrosurgical device, handpiece, or a combination thereof may include a plurality of activation buttons. The plurality of activation buttons may be a first activation button and a second activation button. The one or more buttons may be exposed and/or unlocked by the shuttle as the shuttle moves, the blade moves, or both to and/or from a monopolar configuration to a bipolar configuration or vice versa. For example, the monopolar activation button may only be exposed when the shuttle, blade, or both are in the monopolar configuration. The monopolar activation button, the bipolar activation button, or both may turn on power to the respective electrode so that power is supplied to the area of interest. The activation buttons may be a toggle control button. The toggle control button may toggle between a cut mode, a coagulation mode, or both. The toggle control button may change modes of the forceps. The toggle control button may toggle between different strengths of the electromagnetic latching system (i.e., an amount of force applied by the electromagnetic latching system). The surgical forceps may include power and may be part of an electrosurgical device.

The electrosurgical device and associated componentry may be part of an electrosurgical system. The electrosurgical system may be any system that includes one or more of the devices taught herein. Preferably, the electrical surgical system includes at least an electrosurgical device. The electrosurgical system may include one or more handpieces as taught herein, one or more ground pads, one or more generators, one or more electrosurgical devices, one or more adjacent handpiece components, one or more surgical forceps, or a combination thereof and the teachings herein of each device which are incorporated into the electrosurgical system. The electrosurgical device may function to be used by a surgeon to perform a surgical procedure. The electrosurgical device may function to be switched between two or more configurations, two or more states, or both. For example, the electrosurgical device may be switched between a monopolar configuration, a bipolar configuration, a non-electrosurgical configuration, an intermediate configuration, or a combination of the four. The electrosurgical device may be any device that may be switched between two or more configurations with one hand so that a user may switch between the configurations without the need for a second hand, without disrupting the procedure, or both. The electrosurgical device may be any device and/or configuration that may be used ambidextrously, ambidextrously switched between configurations, or both. The electrosurgical device may be used to cut, perform hemostasis, coagulate, desiccate, fulgrate, electrocautery, or a combination thereof. The electrosurgical device may be any device that includes bipolar capabilities, monopolar capabilities, non-electrosurgical capabilities, or a combination thereof. The electrosurgical device may be used in open surgery. In addition to its electrosurgical capabilities the electrosurgical device may be used for non-electrosurgical purposes. For example, the electrosurgical device may be used as forceps, tweezers, or both that may be used to grip an object, an organ, a vein, skin, tissue, the like, or a combination thereof. In another example, one or more parts of the device may include a sharp edge and may be used to cut, similar to that of a scalpel. The electrosurgical system may include a handpiece and a generator. One or more therapy signals may extend between the handpiece and the generator; be created by the generator and provided to the handpiece, surgical forceps, electrosurgical device, or a combination thereof for application to location of interest; or both.

The one or more therapy signals may be a signal, power, continuity, or a combination thereof. The one or more therapy signals may extend from the handpiece to the generator or vice versa. The one or more therapy signals may be formed by the handpiece, formed by the generator, or both. The electrosurgical therapy signals may be a therapy current. Preferably, the electrosurgical therapy signals indicate that a user has performed a step and a signal is being transmitted so that therapy current, energy, or both is generated. The electrosurgical therapy signals may provide a signal so that one or more therapy currents are produced and the therapy currents may be used for electrosurgery. The electrosurgical therapy signal may be a monopolar therapy signal, a bipolar therapy signal, or both. The monopolar therapy signal may be any signal that has a voltage differential between a return port and an active port in the generator. The monopolar therapy signal may be any signal that when applied by the electrosurgical device extends from one pole of an electrosurgical device to another pole located at a remote location (e.g., a remote electrode or ground pad), off of the electrosurgical device, off the handpiece, or a combination thereof. The bipolar therapy signal may be any signal that has a voltage differential between two leads that are connected to the electrosurgical device, that are located in the generator, or both. The bipolar therapy signal may be any signal that when applied by the electrosurgical device extends from one component of a handpiece to another component of the handpiece (e.g., between two working arms, from a blade electrode to one or both working arms, or both). An electrosurgical therapy signal may exit the handpiece so that a therapy current extends from a blade electrode, between the first working arm and the second working arm, between the blade electrode and one or both of the working arms, or a combination thereof. The therapy signal may be generated and conducted between the handpiece to the generator.

The generator may be any device that supplies power, a therapy current, control signals, an electrosurgical therapy signal, electronically reconfigures itself in response to a signal from the user, physically reconfigures in response to adjustments by the user, or a combination thereof. The generator may function to be electrically connected to a handpiece to provide and/or receive electrosurgical therapy signals, power, therapy current, electromagnetic energy (i.e., energy that powers the electromagnetic latching system) or a combination thereof. The generator may be capable of producing only a single therapy current. The generator may be capable of producing two therapy currents. The generator may include two or more power connections, three or more power connections, or four or more power connections. The generator may include one or more switches that may be switched between one or more of the power connections so that power, signals, or both may be selectively applied to the electrosurgical device based upon a desired configuration of the electrosurgical device. The generator may include a central processing unit (CPU), a series of internal switching, or both. The CPU, internal switching, or both may be used to switch the electrosurgical device between a first configuration, a second configuration, a third configuration, a monopolar configuration, a bipolar configuration, a non-electrosurgical configuration, or a combination thereof. The two opposing working arms may be configured as forceps and each working arm may include an active portion.

The active portion may function to apply power. The active portion may be the same portion as the contact regions of the forceps. Thus, for example, when tissue is grasped between the contact portions of the forceps, power may be supplied to the tissue through this contact portion. The active portion of the working arms preferably is between the two opposing working arms and the active portion of the blade (i.e., blade electrode) is the portion that extends beyond the working arms, flush with the distal ends of the working arms, or both. The active portions may be substantially surrounded by inactive portions or portions that are insulated. The inactive portion may be any portion that does not supply power, that is insulated, or both. The inactive portion may be any portion that may transfer power through incidental contact and thus are insulated so that incidental transfer of power does not occur and/or stray current is prevented. The inactive portion may be an insulating material, a housing, or both.

The working arms may be located within a housing. The housing may be any part of the device that may include one or more working arms and be gripped by a user during use. The housing may electrically connect, mechanically connect, or both the two working arms. The housing may be a movable connection (e.g., a pivot point) so that the two working arms may be moved when the housing is compressed. The housing may substantially surround the working arms so that only the tip regions (e.g., electrodes) extend out of the housing and are exposed. The housing may surround an outer side of the working arms and an inner side of the working arms may be exposed so that as the blade is extended between the two working arms, the blade contacts one or both of the working arms, or both. The housing may include a gripping portion. The gripping portion, upon an application of pressure, may close the working arms and upon a release of pressure the working arms may return to an open position. The gripping portion may assist the user in holding the electrosurgical device like a pencil or probe. The gripping portion may include one or more electromagnetic activation buttons. The electrosurgical device may include an outer housing and an internal housing. The internal housing may include, surround, encapsulate, encase, house, or a combination thereof, one or more internal features of the electrosurgical device. The housing may be electrically connected to a power source and provide power to each of the working arms. The housing may be electrically insulating. The housing may include one or more movable connections (e.g., hinges and/or one or more hinge portions).

The one or more movable connections when configured as hinges may function to connect rigid pieces, impart flexibility into the working arms, the handpiece, the electrosurgical device, preferably the forceps, or a combination thereof. The one or more movable connections when configured as hinges may function as a pivot point as discussed herein. The one or more hinges may function to impart movement into the housing of the forceps while allowing the housing to substantially cover the components of the forceps. There may be a hinge on only one working arm, a hinge on each working arm, or a hinge that connects the working arms. The housing of the forceps may include a rigid section, a stationary section, a movable section, a flexible hinge section, or a combination thereof. The rigid section, the stationary section, or both may be on a proximal end of the electrosurgical device (i.e., closest to the user). The rigid section or stationary section (e.g., central section) may not move when the working arms are moved. The hinge may create a pivot point for a movable section to rotate about or move about. The hinge may be a connection point for a deflecting beam. For example, the working arms may form a cantilever connection and the working arms may move about the connection so that the working arms may be moved together, moved apart, or both. The movable section may function to move so that a gripping force, a gripping movement, or both are created. The movable section may cover all or a portion of the working arms. The working arms may be the movable section of the forceps. The movable section may connect to a stationary section or a rigid section and the movable section may move relative to the stationary section, the movable section, or both. Only a tip of the working arm may extend beyond the movable section of the housing. The movable section may be substantially rigid but may move about a movable connection so that the section is movable and/or flexible. For example, the movable section of the working arm itself may not be flexible but the arm may move about the movable connection so that the arm is movable. The movable section may be the portion of the forceps that is moved during use and the movable section may move relative to a stationary section, a rigid section, or both about the movable connection.

The movable connection may function to allow a hinging action, movement back and forth (i.e., lateral direction), or both. The movable connection may create a force (e.g., a biasing force) that opposes a gripping of the forceps so that the forceps default open or to a neutral position; is in the direction of gripping so that the forceps default closed or to a neutral position; or a combination of both. The neutral position may be where the working arm are spread apart with a gap between the working arms or the arms are closed. The movable connection may create the resilient moving forces. The movable connection may be free of generating forces or storing energy. For example, the movable connection may allow for movement of components and a biasing device may move the components. The movable connection may create a pivot point that opposes a rigid connection or a rigid portion (e.g., central section). The movable connection may include a pin that one or both of the working arms rotate or move about. The movable connection may be free of a pin. The movable connection may be a location of deflection such as a deflecting beam or a cantilever segment that deflects. The rigid section may remain static while the movable section moves about the rigid section. The rigid section may form a side of the movable connection that anchors the movable section so that the movable section may move, flex, pivot, or a combination thereof. The movable section may be any shape so that the movable section moves. The movable section may be restrained my one or more securing mechanism, one or more electromagnetic latching systems, or both.

The one or more immobilization arms, one or more immobilization features, or both may be any feature of the housing, the working arms, or both that may immobilize one or both working arms when the forceps are moved to a monopolar configuration, when the forceps are gripping a feature of interest, or both. The immobilization arms may be connected to the housing and extend between one or both of the working arms and when the blade is advanced the immobilization arms are separated and the working arms are moved into contact with each other and secured. The immobilization arms may be connected to the housing and extend between one or both of the working arms and when the blade is advanced the immobilization arms are compressed, pushed together, or both and the working arms are moved into contact with each other and secured. The immobilization arms may be one example of a securing mechanism that may be used to mechanically lock or secure the working arms in a closed position. The housing, the working arms, or both may be free of immobilization arms.

The two or more working arms may be immobilized by one or more securing mechanisms, the one or more electromagnetic latching systems, or both. The one or more securing mechanism, electromagnetic latching systems, or both may be an immobilization feature. The immobilization feature may be any feature that connects the two or more working arms together so that the arms are immobilized in the monopolar configuration, so that the forceps are disabled, or both. The immobilization features may be part of the arms, part of the housing, all or a part of the shuttle, or a combination thereof. The immobilization features may include a track that extends along all or a portion of each arm and as the shuttle is moved forward or backward to the monopolar configuration, each track may extend into communication with the shuttle so that each of the working arms are moved into contact with each other and vice versa from the bipolar configuration. The immobilization feature may be a piece that slides and compresses the working arms, a piece that twists and radially compresses the working arms, or a combination of both. The immobilization feature may be a wedge that extends between two features of the forceps and prevents movement of the working arms. The immobilization feature while being moved and immobilizing may move a blade, may extend a blade between the working arms, or a combination of both. The immobilization features are one example of a securing mechanism.

The securing mechanism may function to lock the first working arm and the second working arm so that the first working arm and the second working arm are not movable relative to each other. The securing mechanism may lock a blade between the first working arm and the second working arm. The securing mechanism may be laterally movable with the working arms and may form a connection any time the working arms are pressed together. The securing mechanism may mechanically, electrically, or both connect the first working arm to the second working arm. The securing mechanism may directly or indirectly connect the first working arm and the second working arm together. For example, a device may extend between the first working arm and the second working arm and prevent the working arms from moving relative to each other. The securing mechanism may include features on the first working arm, the second working arm, or both. The securing mechanism may include one or more devices that extend from the first working arm to the second working arm. The securing mechanism may be an electromagnetic latching system.

The electromagnetic latching system functions to move the working arms relative to each other, lock the working arms, reduce an amount (i.e., magnitude) of force required to move the working arms, increase an amount of force required to move the working arms, or a combination thereof. The electromagnetic latching system may act as a biasing device. The electromagnetic latching system may use magnets to move the working arms. The electromagnetic latching system may use a magnetic field to move the working arms or assist in moving the working arms. The electromagnetic latching system may be all "on," or all "off." Preferably, the electromagnetic latching system provides an adjustable amount of force. The amount (i.e., magnitude) of force applied may be in the same direction and/or an opposing direction as the resilient moving force of the working arms. The amount (i.e., magnitude) of force applied may be superimposed (i.e., superposition of forces) upon the resilient moving force of the working arms. The superposition of forces may laterally to move the working arms together, laterally to move the working arms apart, laterally to assist a user in moving the working arms apart or together. The superposition of forces may act only when an electromagnetic activation button is depressed. The resilient moving force may be a force that moves the working arms apart from each other until they reach a neutral state, toward each other until they reach a neutral state, or both. For example, the resilient moving force may be generated by a biasing device or the elasticity of the working arms elastically deforming to the neutral state. The resilient moving force may move the jaws apart or open the jaws (i.e., resilient opening force), move the jaws towards each other or close the jaws (i.e., resilient closing force), or both. The resilient moving force may vary depending upon a direction or magnitude of a force moving the first working arm, the second working arm, or both. The resilient moving force may be a force that is caused by storing energy as an external force is applied. The resilient moving force may be a mechanical force that is created by movement of the working arms from a neutral state. The resilient moving force may created by a bias device, a movable connection, or both. The electromagnetic latching system may be adjustable by adjusting the strength of the electromagnetic field provided by one or both of the working arms. The magnitude of force applied to the working arms may be varied by the electromagnetic latching system. As discussed herein all magnitudes are discussed in the positive. For example, the working arms are moved towards each other or are moved away from each other. Although these directions are opposing directions, the directions are both recited as a positive magnitude. The magnitude of force applied by the electromagnetic latching system may be varied based upon an impedance measurement, impedance calculation, or both. The magnitude of force may be based upon a measurement of impedance of tissue held between the first working arm and the second working arm. As the impedance increases or decreases the amount of force applied may be increased or decreased. Preferably, as the impedance increases the amount of force applied increases. The electromagnetic latching system may not apply any forces when off and the forceps may be used normally without any increase or decrease of forces by the forceps. The electromagnetic latching system may include one or more electromagnetic latches and preferably a plurality of electromagnetic latches.

The one or more electromagnetic latches may function to move the working arms relative to each other or to prevent movement of the working arms relative to each other. The electromagnetic latches may assist in moving the working arms relative to each other. The electromagnetic latches may only work when power is applied. The electromagnetic latches may receive power and create an electric field that assists in moving the working arms. The electromagnetic latches may be located in the first working arm, the second working arm, or both working arms. A plurality of electromagnetic latches may be located in the first working arm, the second working arm, or both. The electromagnetic latches may be located across from a magnetic material so that only one electromagnetic latch is needed per device. For example, the electromagnetic latch may be located in the first working arm and a material that attracts or repels the electromagnetic latch may be located across from the electromagnetic latch so that when the electromagnetic latch is activated the working arms are moved relative to each other. The material that attracts or repels may be any material that is affected by magnetic fields. The material may be iron, nickel, cobalt, iodestone, ainico, or a combination thereof. The electromagnetic latch may include a power coil that when activated creates an electromagnetic field. The power applied to the electromagnetic latch may be a first polarity to move the working arms towards each other and in a second polarity to move the working arms apart from each other. The power applied to the electromagnetic latch may be increased or decreased to increase or decrease the magnitude of force applied by the electromagnetic latch. The magnitude of force applied by the electromagnetic latch may be increased or decreased by turning on or off one or more of the electromagnets located within each electromagnetic latch. Each electromagnetic latch may include one or more electromagnets. Each electromagnetic latch may include a plurality of electromagnets. For example, each electromagnetic latch may include 5 electromagnets and depending on the variable setting by the user only 1, 2, or 3 or more of the electromagnetic may be activated. In a full power setting all 5 magnets may be activated. In another example, each working arm may include a coarse electromagnetic latch that is always in operation and a fine electromagnetic latch may be turned on that provides for fine adjustment of the amount of force being applied. The electromagnetic latch may lock the working arms together, the blade between the working arms, or both. The electromagnetic latch may lock the working arms to the blade so that the working arms and the blades are all immobilized. The electromagnetic latch may move the working arms so that a mechanical latch may lock the working arms together using one or more mechanical devices. The one or more devices may be a resilient tongue that extends from the first working arm to the second working arm.

The resilient tongue may function to extend between and connect the first working arm and the second working arm together. The resilient tongue may prevent movement of the first working arm relative to the second working arm. The resilient tongue may only be extendable when the blade is retracted, extended, not present, or a combination thereof. The resilient tongue may flex and extend through a slot in the opposing arm to form the connection. The resilient tongue may partially extend through a slot in an opposing working arm. The resilient tongue may have another tongue that extends from a main portion of the resilient tongue and the tongue may form a connection with a latch and this connection may prevent movement of the working arms relative to each other.

The tongue may function to connect or lock the first working arm with the second working arm. The resilient tongue may include one or more tongues. The resilient slider may include a plurality of tongues so that the working arms may be locked in different positions so that the locked position between the first working arm and the second working arm is selectable. The plurality of tongues may allow for the working arms to be selectively positioned relative to each other or the force between the working arms to be selectively chosen. The tongue may form a connection with a slot, a latch slider, an edge of a latch slider, or both. The tongue may project substantially perpendicular to the resilient tongue and form a catch. The tongue may have an angled portion and a flat portion. The angled portion may allow for one way movement. The flat portion may prevent movement of the tongue in a direction (e.g., the working arms laterally apart). The tongue may extend through a slot in an opposing arm.

The slot may function to permit all or a portion of the resilient tongue to extend therethrough to create a locked relationship. The slot may be on an edge of the working arm. The slot may be square, rectangular, circular, oval, symmetrical, non-symmetrical, or a combination thereof. The slot may allow for a tongue to catch a wall of the slot to prevent movement of the working arms. The slot may receive a latch slider and permit the latch slider to prevent movement of the working arms, while a portion of the resilient tongue extends through the slot.

The latch slider may function to restrict movement of the first working arm and the second working arm together. The latch slider may contact a portion of the tongue, resilient tongue, or both and prevent movement of the working arms relative to each other. The latch slider may move between one or more tongues so that the tongues provide selective locking between the first working arm and the second working arm. The latch slider may laterally move, longitudinally move, rotationally move, or a combination thereof to permit the working arms to be selectively locked, released, or both. The latch slider may be a movement mechanism. The movement mechanism may release the forceps from a locked state. The movement mechanism may be a latch slider. The latch slider may contact an edge of the tongue and prevent the tongue and working arms from moving away from each other. The latch slider may assist in the securing mechanism being a selectable mechanical latch. The latch slider and securing mechanism may be used in lieu of or in addition to an arm securing mechanism. However, the electrosurgical device may be free of any securing mechanisms and may include only arm securing mechanism. The latch slider, resilient tongue, securing mechanism, or a combination thereof, may prevent movement of the blade, lock the blade in place in addition to the working arms, be free of interference with the blade so that the blade may be actively moved, or a combination thereof.

The blade may function to apply monopolar power during a procedure, apply bipolar power, that may be longitudinally movable, rotationally movable, extendable, retractable, a mechanical cut, or a combination thereof. The blade may be static. The blade may have a first position (e.g., retracted), a second position (e.g., flush with distal ends of the working arms), and a third position (e.g., extended beyond the distal ends of the working arms). The first position may be where the blade is located relative to the working arms so that the working arms are past (i.e., distal) the blade (e.g., the blade is retracted so that the working arms extend past the blade or the working arms are extended so that the working arms extend past the blade). The second position may be where the distal end of the blade is substantially flush with the distal ends of the working arms (all of the distal ends are within about 3 mm or less, about 2 mm or less, about 1 mm or less, preferably in a straight line (i.e., about 0 mm)). The second position may have the blade located between the working arms and all three may be aligned to create a probe. The third position may be where the blade is located relative to the working arms so that the blade is extended beyond the working arms (e.g., the blade is extended so that the working arms are located proximate to the user relative to a distal end of the blade or the working arms are retracted so that the blade extends beyond the working arms). The third position may be where the blade is electrically connected, supplies a therapy current, is electrically continuous, or a combination thereof. The blade may be moved by a shuttle, a first slider, a second slider, or a combination thereof.

The shuttle may function to cover one or more activation buttons, move one or more activation arms, move the blade, moves one or both working arms, immobilizes and/or electrically disconnects one or more features of the electrosurgical device, immobilizes one or more activation buttons, impedes movement and/or depression of one or more activation buttons, move one or more immobilization arms, one or more electromagnetic activation buttons, or a combination thereof. The shuttle may connect two or more sliders. The first and second slider may move the working arms, blade, or both between the various positions and configurations discussed herein. The shuttle may be a slider assembly that moves the blade. The shuttle, the working arms, or both may be moved or prevented from moving by one or more bias devices.

The bias device may be any device that may act to move, retract, advance, a combination thereof one or more components of the electrosurgical device. For example, the bias device may move the working arms to a neutral state when compressed to grip or spread apart to increase the distance between working arms. In another example, the bias device may assist in longitudinally moving the blade. The bias device may be an integral part of the forceps, the working arms, or both. For example, the working arms may be a deflecting beam and this deflection may act as a bias device that returns the working arms to a neutral state. The bias device may bias when placed in tension, in compression, or both. The bias device may be a wrap spring that may be placed in tension or in compression. The bias device may wrap around a pin in the pivot point. The bias device may extend between two working arms. The bias device may act to separate the working arms of the electrosurgical device when in the bipolar configuration. The bias device may push the blade and/or shuttle forward into a monopolar configuration, pull the blade and/or shuttle back from a monopolar configuration, or a combination thereof. The bias device may ensure that the shuttle, blade, working arms, monopolar electrode, blade, or a combination thereof are in a fully extended and/or fully retracted state. For example, if a user moves a shuttle towards a forward position and stops short, the bias device may complete the movement to the next position or a final position. The bias device may assist in moving any of the devices and/or features discussed herein so that the devices and/or features are bi-stable or multi-stable. For example, the bias device may ensure that the blade is always in one of the positions discussed here such as fully extended, flush, or fully retracted and not located therebetween. The bias device may be a spring, a piece of rubber, an elastomeric piece, a bend in metal that forms a bias surface, or a combination thereof. If the bias device is bent metal the metal may be bent forming more than one plane. The first plane may contact a first surface and the second arm may contact a second surface so that two opposing electrosurgical components are moved. Preferably, the bias device is a spring that may be stretched and compressed. The bias device may be connected to the blade, a shuttle, between the working arms, or a combination thereof.

Figure 2:
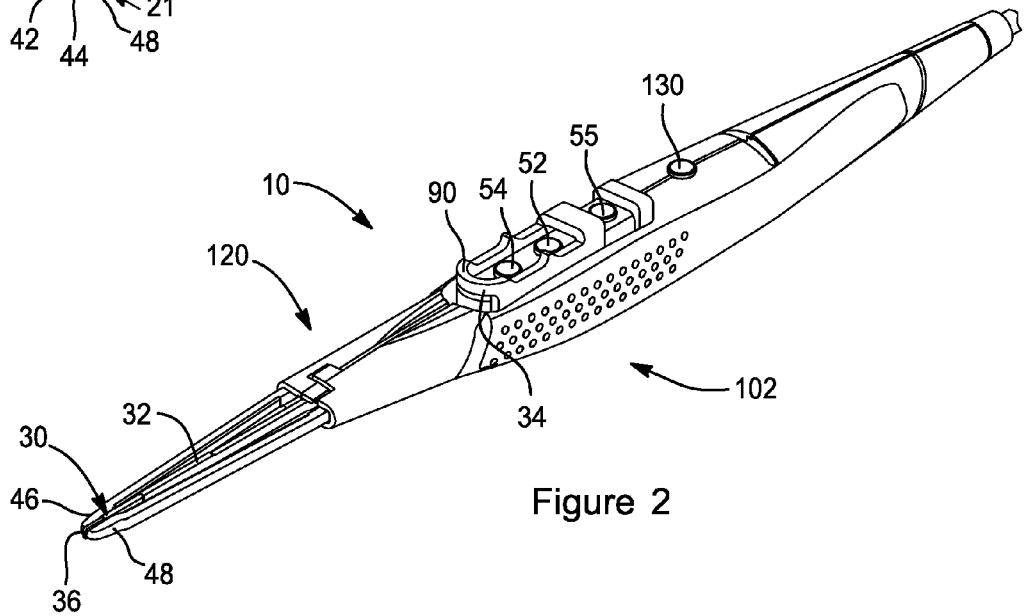
FIG. 2 illustrates the electrosurgical device of FIG. 1 in a second configuration.

FIG. 1 depicts an electrosurgical device 10 comprising a forceps 20 with a central section 26 from which a first working arm (or jaw) 22 having a distal end 46 and a second working arm (or jaw) 24 having a distal end 48 and an advanceable blade 32. A cord 38 extends from the proximal end 28 of the central section 26 and connects the electrosurgical device 10 to an electrosurgical generator (not shown). The first working arms 22 and the second working arm 24 are biased apart from each other. The user can apply finger pressure on the first working arms 22 and the second working arm 24 to cause them to approach each other so as to grasp tissue (not shown). The first working arm 22 and second working arm 24 include a first electrode 42 and a second electrode 44. A first activation button 52 is located on the central section 26. When the user depresses the first activation button 52 the generator (not shown) can provide a first electrosurgical signal. For example, when the user depresses the first activation button 52 the generator produces a bipolar electrosurgical signal and delivers the bipolar electrosurgical signal to the first electrode 42 and the second electrode 44 to produce a bipolar current that passes between the first electrode 42 and the second electrode 44. The characteristics of this electrosurgical current such as voltage, current, power, frequency, and duty cycle, may be configured specifically to coagulate tissue held between the first working arm 22 and second working arm 24. An advanceable blade 32 is located between the first working arm 22 and the second working arm 24. The blade 32 is shown in a first configuration 100 (e.g., bipolar configuration) in which the blade 32 is fully retracted to a proximal position where the distal end 36 is located inside of the distal ends 46, 48 of the working arms 22, 24. In the first configuration 100 the first working arm 22 and the second working arm 24 are free to move in a direction 21 towards each other. The blade 32 is connected to a first slider 34, which is configured as a shuttle 90, that slides the blade 32 distally and proximally along the forceps 20 (see FIG. 2 for a distal position) and locks the working arm together. When the first slider 34 is in its distal position the blade 32 is advanced to an advanced position (FIG. 2). When the first slider 34 is in a proximal position the blade 32 is retracted to a retracted position (FIG. 1). When the first slider 34 is in the proximal position the first working arm 22 with the first electrode 42 and the second working arm 24 with the second electrode 44 are movable toward each other in the direction 21 to grip tissue (not shown) there between. The electrosurgical device 10 includes an electromagnetic latching system 120 that biases the working arms 22, 24 when the electromagnetic activation button 130 is depressed.

FIG. 2 illustrates the blade 32, which includes a blade electrode 30, in a second configuration 102 (e.g., monopolar configuration) which is a partially advanced position (e.g., the distal end of the blade is substantially flush with the distal ends of the working arms). The blade electrode 30 is advanced so that its distal end 26 is flush, or substantially flush, with the distal ends 46, 48 of the first working arm 22 and the second working arm 24. Flush means for the blade to be extended so that the distal end 36 of the blade 32 is aligned with the distal ends 46, 48 of the first working arm 22 and the second working arm 24 or for the distal end 36 of the blade electrode 32 to extend slightly beyond the distal ends 46, 48 of the working arms 22, 24. The total amount of the extension may be approximately 3 mm or less. A toggle control button 55 is exposed by the slider 34 when in its forward position. When the slider 34, which is shown as a shuttle 90, is in a proximal position the exposed cut and coagulation buttons are configured to provide, for example, monopolar cut and monopolar coagulation and when the slider 34 is in a distal position the exposed cut and coagulation buttons 52, 54 may be configured to provide, for example, bipolar cut and bipolar coagulation. The electrosurgical device 10 includes an electromagnetic latching system 120 that biased the working arms 22, 24 to the closed position the electromagnetic activation button 130 was depressed.

Figure 3:
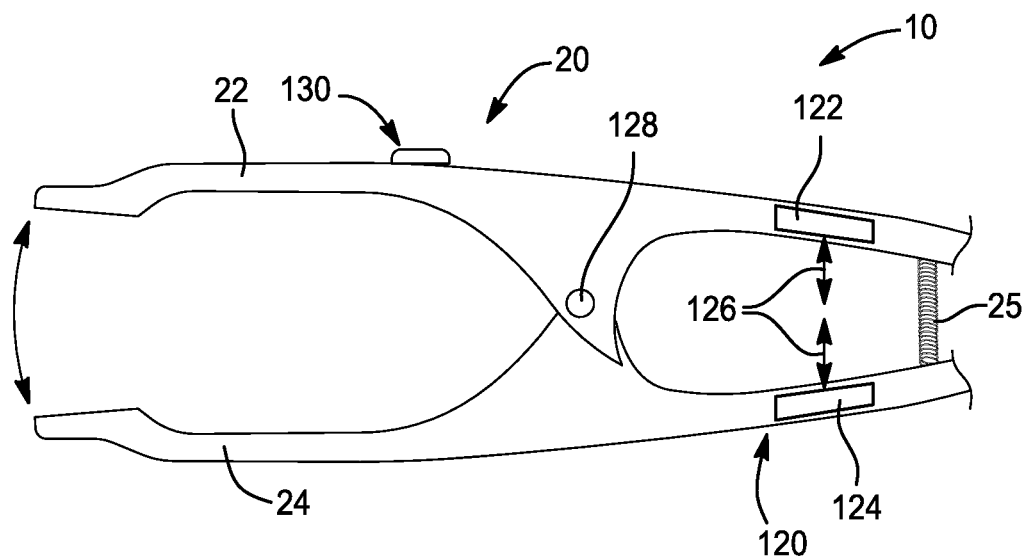
FIG. 3 illustrates a side view of an electrosurgical device including an electromagnetic latching system in a proximal position.

FIG. 3 illustrates a side view of an electrosurgical device 10 that includes forceps 20 with a first working arm 22 and a second working arm 24. The forceps 20 include an electromagnetic latching system 120 that assists in biasing the first working arm 22 and the second working arm 24 towards each other, away from each other, or both. As shown, the electromagnetic latching system 120 has a first electromagnetic latch 122 in the first working arm 22 and a second electromagnetic latch 124 in the second working arm 24 with both of the electromagnetic latches being located behind (i.e., proximal) a movable member shown as a pivot point 128. During operation the first electromagnetic latch 122 is repelled from the second electromagnetic latch 124 so that a gripping force is created and the polarity may be reversed so that the first electromagnetic latch 122 and the second electromagnetic latch 124 are attracted to each other and the jaws are opened. The electromagnetic latching system 120 moves the forceps in the direction 126 when the electromagnetic activation button 130 is depressed. A bias device 25 is located between the first working arm 22 and the second working arm 24. The bias device 25 biases the first working arm and the second working arm so that a neutral position is maintained between the working arms 22, 24 when no external forces are being applied such as by the electromagnetic activation buttons 130.

Figure 4A:
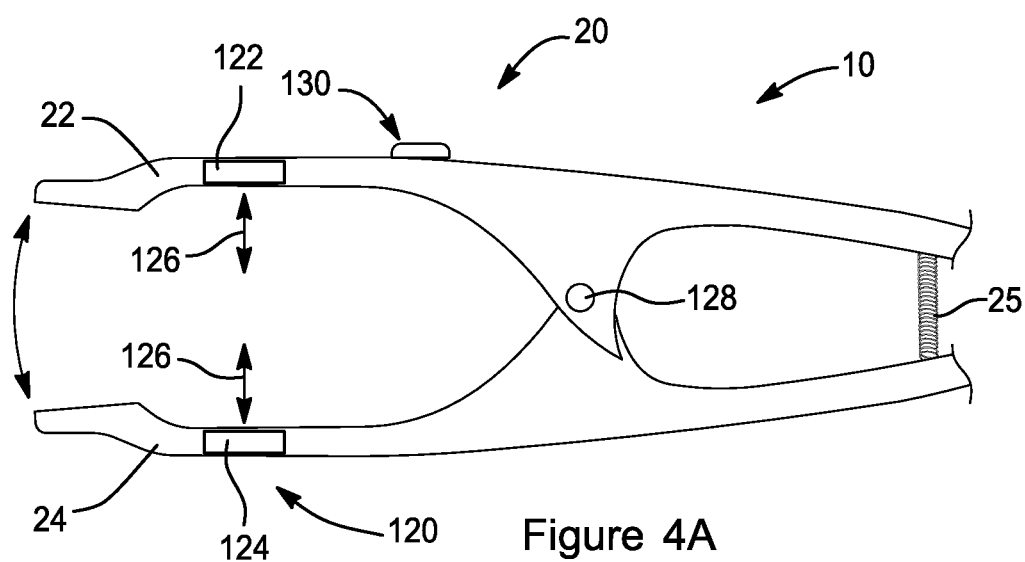
FIG. 4A illustrates a side view of forceps including a biasing device, and an electromagnetic latching system in a distal position.

FIG. 4A illustrates a side view of an electrosurgical device 10 that includes forceps 20 with a first working arm 22 and a second working arm 24. As shown, the electromagnetic latching system 120 has a first electromagnetic latch 122 in the first working arm 22 and a second electromagnetic latch 124 in the second working arm 24, with both the electromagnetic latches being located in front (i.e., distal) of a pivot point 128. During operation the first electromagnetic latch 122 is attracted to the second electromagnetic latch 124 so that a gripping force is created and the polarity may be reversed so that the first electromagnetic latch 122 and the second electromagnetic latch 124 are repelled from each other and the jaws are opened. The electromagnetic latching system 120 moves the forceps in the direction 126 when the electromagnetic activation button 130 is depressed. A bias device 25 is located between the first working arm 22 and the second working arm 24. The bias device 25 biases the first working arm and the second working arm so that a neutral position is maintained between the working arms 22, 24 when no external forces are being applied such as by the electromagnetic activation buttons 130.

Figure 4B:
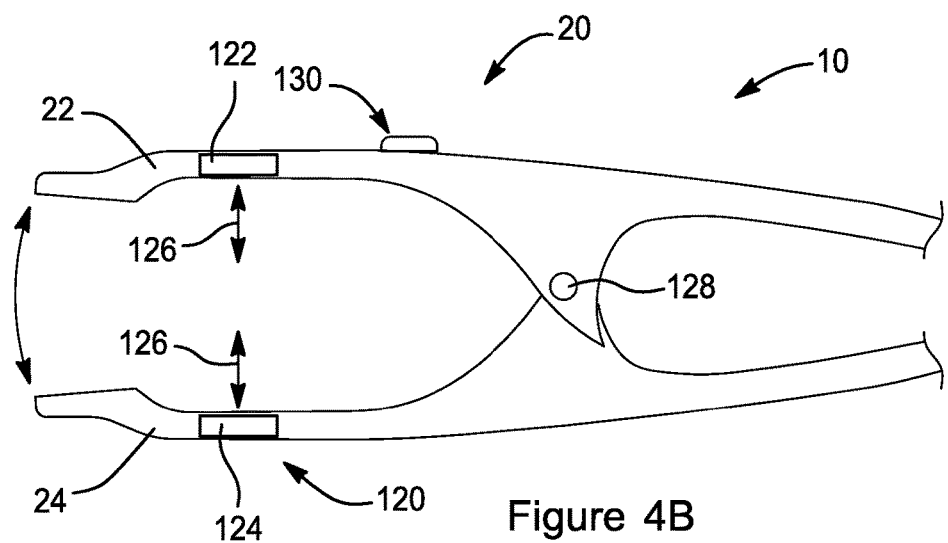
FIG. 4B. illustrates a side view of forceps including an electromagnetic latching system in a distal position.

FIG. 4B illustrates a side view of an electrosurgical device 10 that includes forceps 20 with a first working arm 22 and a second working arm 24. As shown, the electromagnetic latching system 120 has a first electromagnetic latch 122 in the first working arm 22 and a second electromagnetic latch 124 in the second working arm 24, with both the electromagnetic latches being located in front (i.e., distal) of a pivot point 128. During operation the first electromagnetic latch 122 is attracted to the second electromagnetic latch 124 so that a gripping force is created and the polarity may be reversed so that the first electromagnetic latch 122 and the second electromagnetic latch 124 are repelled from each other and the jaws are opened. The electromagnetic latching system 120 moves the forceps in the direction 126 when the electromagnetic activation button 130 is depressed. As shown the working arms 22, 24 have a resilient opening force and the working arms 22, 24 open without an application of any external forces.

Figure 5:
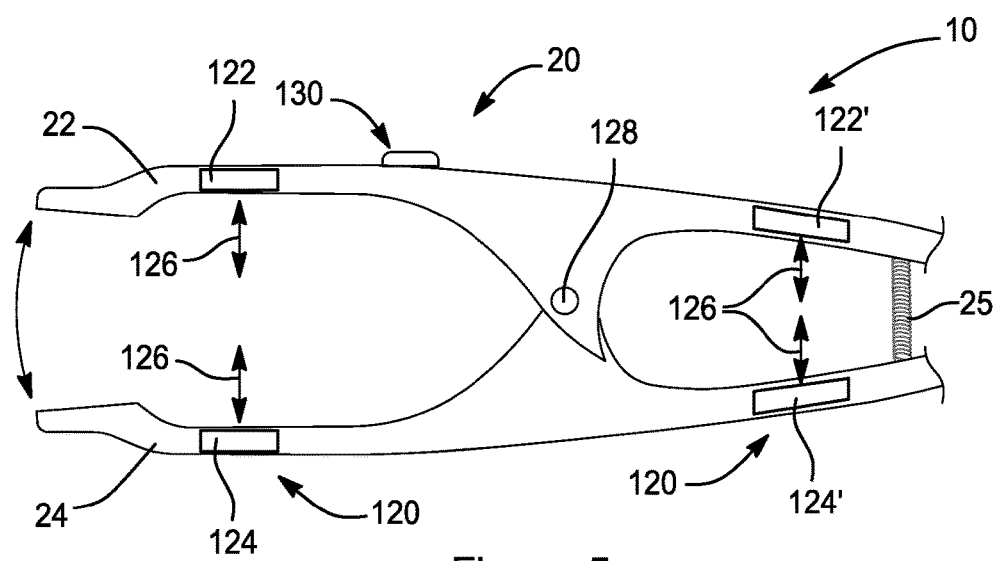
FIG. 5 illustrates a side view of an electrosurgical device including electromagnetic latching system in a proximal position and a distal position.

FIG. 5 illustrates a side view of an electrosurgical device 10 including forceps 20 with a first working arm 22 and a second working arm 24 that are connected together by a pivot point 128. An electromagnetic latching system 120 is located distal of the pivot point 128 and one is proximal of the pivot point. Each of the electromagnetic latching systems 120 include a first electromagnetic latch 122, 122' on the first working arm 22 and a second electromagnetic latch 124, 124' on the second working arm 24. The electromagnetic latching systems 120 move the forceps 20 in the direction 126. During operation, one of the electromagnetic latching systems 120 provide course control (or a constant force) and the second of the electromagnetic latching system provide fine control (or a variable control to vary the amount of force required by the user). For example, the first set of electromagnetic latches (122, 124) may bias the working arms towards and away from each other and the second set of electromagnetic latches (122', 124') may allow for the amount of force required to be increased or decreased to accommodate a surgeon's desire. The electromagnetic latching system 120 assists in moving the working arms 22, 24 in the directions 126 when the electromagnetic activation button 130 is depressed.

Figure 6:
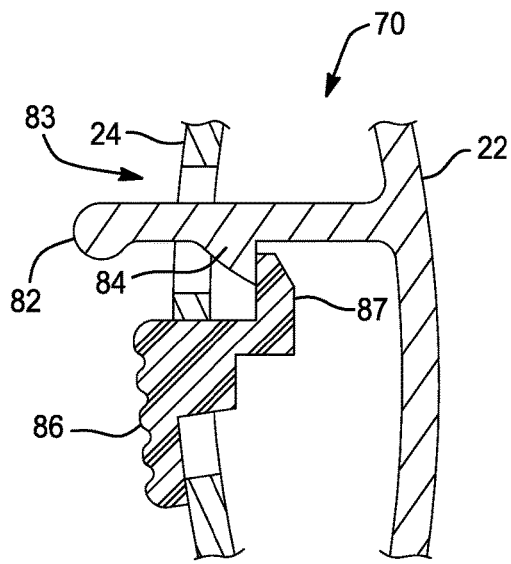
FIG. 6 illustrates a close-up view of a securing mechanism connecting two working arms.

FIG. 6 illustrates a securing mechanism 70. The securing mechanism 70 is located between the first working arm 22 and the second working arm 24 so that the working arms are secured together. The securing mechanism 70 includes a resilient tongue 82 that extends through a slot 83 in the second working arm 24. A tongue 84 extends from the resilient tongue 82 and the tongue 84 contacts a front end of a latch slider 87 that extends from a latch slider 86. The latch slider 86 is movable so that the tongue 82 and front end of the latch slider 87 are disconnected and the first working arm 22 and second working arm 24 are released so that they are movable relative to each other.

Figure 7:
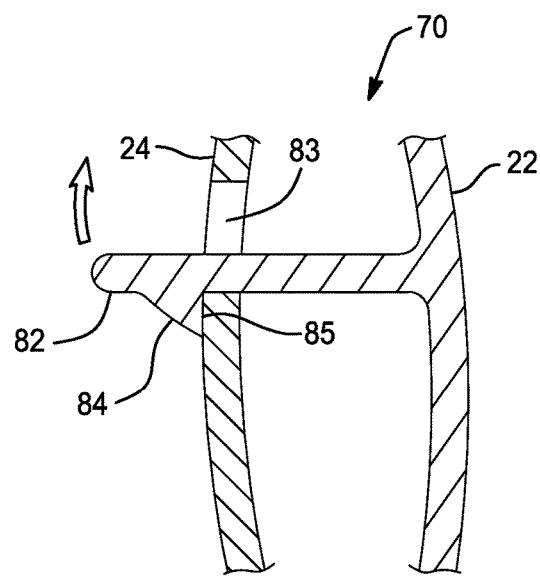
FIG. 7 illustrates a close-up view of a securing mechanism connecting two working arms.

FIG. 7 illustrates a first working arm 22 including a resilient tongue 82 with a tongue 84 that extends from the resilient tongue 82. The second working arm 24 includes a slot 83 that the resilient tongue 82 extends through. The tongue 84 of the resilient tongue 82 is biased into contact with an edge 85 of the slot 83 so that the first working arm and second working arm are connected together and the first working arm 22 and second working arm 24 are secured together.

Figure 8:
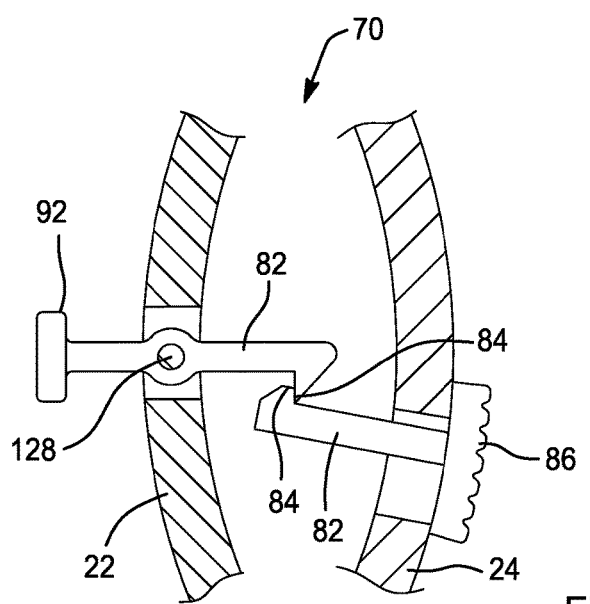
FIG. 8 illustrates a close-up view of a securing mechanism connecting two working arms.

FIG. 8 illustrates a first working arm 22 and a second working arm 24 that each include a portion of a securing mechanism 70. The first working arm 22 includes a resilient tongue 82 that has a movement mechanism 92 located on the outside and a tongue 84 located on the inside with a pivot point 128 there between. The second working arm 24 includes a resilient tongue 82 with a latch slider 86 on the outside and a tongue 84 located on the inside. The tongue 84 of the first arm 22 and the second arm 24 latch together to form a secure connection between the first working arm 22 and the second working arm 24 and the latch slider 86 releases the secure connection so that the first working arm 22 and second working arm 24 are movable relative to each other.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps. By use of the term "may" herein, it is intended that any described attributes that "may" be included are optional.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

We claim:

1. A surgical forceps comprising:
a first working arm and a second working arm configured to move in a direction that is towards each other and a direction away from each other, and the first working arm and the second working arm are movable in the direction towards each other or the direction away from each other, in a manner that creates a resilient moving force;
an electromagnetic latching system including two or more electromagnetic latches;
wherein the electromagnetic latching system is configured to create a force that is superimposed upon the resilient moving force, wherein the force comprises one or more of the following:
(i) the force biases the first working arm, the second working arm, or both in a direction of the resilient moving force; or
(ii) the force biases the first working arm, the second working arm, or both in an opposite direction as the resilient moving force; and
wherein a bipolar current extends between the first working arm and the second working arm and the force is created when a first activation button is energized; and
wherein the electromagnetic latching system has fine adjustment by a first of the two or more electromagnetic latches creating the force and a second of the two or more electromagnetic latches creating one or more adjustable forces that are applied in a same direction, an opposite direction, or both as the force forming an adjusted force so that the adjusted force assists a user in moving the first working arm and the second working arm together or apart.

2. The surgical forceps of claim 1, wherein the surgical forceps are configured to measure impedance of tissue held between the first working arm and the second working arm and the force is based upon a measurement of the impedance of the tissue held between the first working arm and the second working arm.

3. The surgical forceps of claim 1, wherein the two or more electromagnetic latches are located in or on the first working arm, the second working arm, or both.

4. The surgical forceps of claim 1, wherein the two or more electromagnetic latches are only located on the first working arm and a magnetic material is located on the second working arm.

5. The surgical forceps of claim 3, wherein two one or more electromagnetic latches are connected to power from a power source so that when power is applied, each of the two or more electromagnetic latches create the force or the one or more adjustable forces so that the first working arm and second working arm are biased towards each other; the first working arm and the second working arm are biased apart; or both.

6. The surgical forceps of claim 5, wherein the two or more electromagnetic latches are two electromagnetic latches on the first working arm, the second working arm, or both.

7. The surgical forceps of claim 6, wherein the two or more electromagnetic latches are located on the first working arm, the second working arm, or both and the first electromagnetic latch has a constant magnetic field and the second electromagnetic latch has a variable magnetic field so that an amount of force required to move the first working arm and second working arm apart, together, or both is variable by a user.

8. The surgical forceps of claim 3, wherein the two or more electromagnetic latches are located on the first working arm, and a magnetic material is located on the second working arm, wherein the two or more electromagnetic latches are connected to power so that when the power is applied, the two or more electromagnetic latches create the force or the one or more adjustable forces and bias the first working arm and the second working arm.

9. The surgical forceps of claim 1, wherein the first working arm and the second working arm include a neutral position and when the first working arm and second working arm are moved towards each other the resilient moving force is created by the first working arm and the second working arm storing energy so that the first working arm and second working arm return to the neutral position.

10. The surgical forceps of claim 1, wherein a mechanical latch is located in or on the first working arm, the second working arm, or both and the mechanical latch connects the first working arm and the second working arm together so that the electromagnetic latching system can be turned off and the surgical forceps be retained in a closed position.

11. The surgical forceps of claim 1, wherein the first working arm and second working arm are free to move in the direction towards each other so as to grasp tissue therebetween when the electromagnetic latching system is not activated and energized, and the first working arm and second working arm are biased towards each other by the force when the electromagnetic latching system is activated and energized.

12. The surgical forceps of claim 1, wherein the force is adjusted by an adjustment element on the surgical forceps.

13. A surgical forceps comprising:
a first working arm and a second working arm configured to move towards and away from each other; and
an electromagnetic latching system including two or more electromagnetic latches;
wherein the electromagnetic latching system is configured to create a force that is in a direction aligned with closing of the forceps or opposite to the closing of the forceps and a bipolar current that passes between the first working arm and the second working arm when an activation button is depressed and
wherein the electromagnetic latching system has fine adjustment by a first of the two or more electromagnetic latches creating the force and a second of the two or more electromagnetic latches creating one or more adjustable forces that are applied in a same direction, an opposite direction, or both as the force forming an adjusted force so that the adjusted force assists a user in moving the first working arm and the second working arm together or apart.

14. The surgical forceps of claim 13, wherein the force by the electromagnetic latching system opposes the closing of the forceps.

15. The surgical forceps of claim 13, wherein the force by the electromagnetic latching system is in a direction aligned with the closing of the forceps.

16. The surgical forceps of claim 1, wherein the resilient moving force is created by elasticity of the working arms elastically deforming to a neutral state.

17. A surgical forceps comprising:
a first working arm and a second working arm configured to move in a direction that is towards each other and a direction away from each other and the first working arm and the second working arm are movable in the direction towards each other or the direction away from each other, in a manner that create a resilient moving force;
an electromagnetic latching system including two or more electromagnetic latches;
wherein the electromagnetic latching system is configured to create a force that latches the first working arm and second working arm;
wherein a bipolar current extends between the first working arm and the second working arm and the force is created when a first activation button is energized; and
wherein the electromagnetic latching system has fine adjustment by a first of the two or more electromagnetic latches creating the force and a second of the two or more electromagnetic latches creating one or more adjustable forces that are applied in a same direction, an opposite direction, or both as the force forming an adjusted force so that the adjusted force assists a user in moving the first working arm and the second working arm together or apart.

18. The surgical forceps of claim 17, wherein the resilient moving force is created by elasticity of the working arms elastically deforming to a neutral state.

19. The surgical forceps of claim 17, wherein the forceps include a dial that increases or decreases an amount or magnitude of the force applied by the two or more electromagnetic latches.

* * * * *